United States Patent [19]

Hesse

[11] Patent Number: Plant 6,776

[45] Date of Patent: May 2, 1989

[54] CHRYSANTHEMUM PLANT NAMED BRONCO

[75] Inventor: Peter S. Hesse, Bradenton, Fla.

[73] Assignee: Ball Seed Company, West Chicago, Ill.

[21] Appl. No.: 139,763

[22] Filed: Dec. 30, 1987

[51] Int. Cl.[4] ..... A01H 5/00

[52] U.S. Cl. ..... Plt./79

[58] Field of Search ..... Plt./79

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Bronco having dark orange bronze ray florets, large decorative flower type, semi-upright and compact growth habit, free branching and free flowering, and 7 week flower response.

1 Drawing Sheet

The present invention comprises a new and distinct cultivar of *Chrysanthemum morifolium,* hereinafter referred to by the cultivar name Bronco.

Bronco is a product of a planned breeding program which had the objective of creating new Chrysanthemum cultivars having compact habit, early flower response, large bronze decorative flowers, and suitability for production as a garden mum. Such traits in combination were not present or needed improvement in previously available commercial cultivars.

Bronco was originated from a hybridization made by applicant in a controlled breeding program in Parrish, Fla. in 1984. The female parent was Sunny Morning. The male parent of Bronco was Minnautumn. Bronco was discovered and selected as one flowering plant within the progeny of the stated parentage by applicant in November 1984 in a controlled environment in Parrish, Fla.

The first act of asexual reproduction of Bronco was accomplished when vegetative cuttings were taken from the initial selection in March 1985 in a controlled environment in Parrish, Fla. by a technician working under formulations established and supervised by applicant. Horticultural examination of selected units initiated in September 1985 has demonstrated that the combination of characteristics as herein disclosed for Bronco are firmly fixed and are retained through successive generations of asexual reproduction.

The following traits have been repeatedly observed and are determined to be basic characteristics of Bronco, which in combination distinguish this Chrysanthemum as a new and distinct cultivar:

1. Seven week flower response.
2. Dark orange-bronze flower color.
3. Large decorative type flowers.
4. Ray florets are up to 2.8 cm long and 8 mm in width.
5. Total flower diameter reaches 55–60 mm.
6. Semi-upright, compact growth habit.
7. Free branching and free flowering.
8. Suitable for use as a garden mum for production in 4½" to 1 gallon containers.

Bronco has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

Of the many commercial cultivars known to the present inventor, the most similar in comparison to Bronco is Cougar, disclosed in U.S. Plant Pat. No. 4,752. In comparison to Cougar, Bronco has darker bronze flower color, smaller flower size, and is one week earlier flowering in the South. The natural season flower response (mid-season) and flower type of Bronco are similar to those same characteristics of Cougar.

The accompanying photographic drawings show typical inflorescence and foliage characteristics of Bronco. The photographic drawing comprises a black and white photograph with a few flowers in color showing the true flower color of Bronco.

In the following description, color references are made to The Royal Horticultural Society Colour Chart. The color values were determined between 11:00 and 11:30 a.m. on Oct. 21, 1987 under fluorescent light at Parris, Fla.

Classification:

*Botanical.*—*Chrysanthemum morifolium,* cv. Bronco.

*Commercial.*—Decorative garden mum.

INFLORESCENCE

A. Capitulum:

*Form.*—Flat.

*Type.*—Double.

*Diameter across face.*—55–60 mm.

B. Corolla of ray florets:

*Color (general tonality from a distance of three meters).*—Orange-bronze.

*Color (upper surface).*—170A.

*Color (under surface).*—and outside of generally tubular florets prior to opening 162A.

C. Corolla of disc florets:

*Color (mature).*—Yellow.

*Color (immature).*—Yellow-green.

D. Reproductive organs:

*Androecium.*—Present in disc florets only.

*Gynoecium.*—Present in both disc and ray florets.

PLANT

A. General appearance:

*Height.*—Approximately 23 cm when grown in the ground, given no long days and one pinch.

Height will vary depending upon growing conditions.

B. Foliage:

*Color* (*upper surface*).—147A.

*Color* (*lower surface*).—147B.

*Shape.*—Ovate, deeply lobed and serrate margins.

I claim:

1. A new and distinct cultivar of Chrysanthemum plant named Bronco, as illustrated and described, and parts thereof.

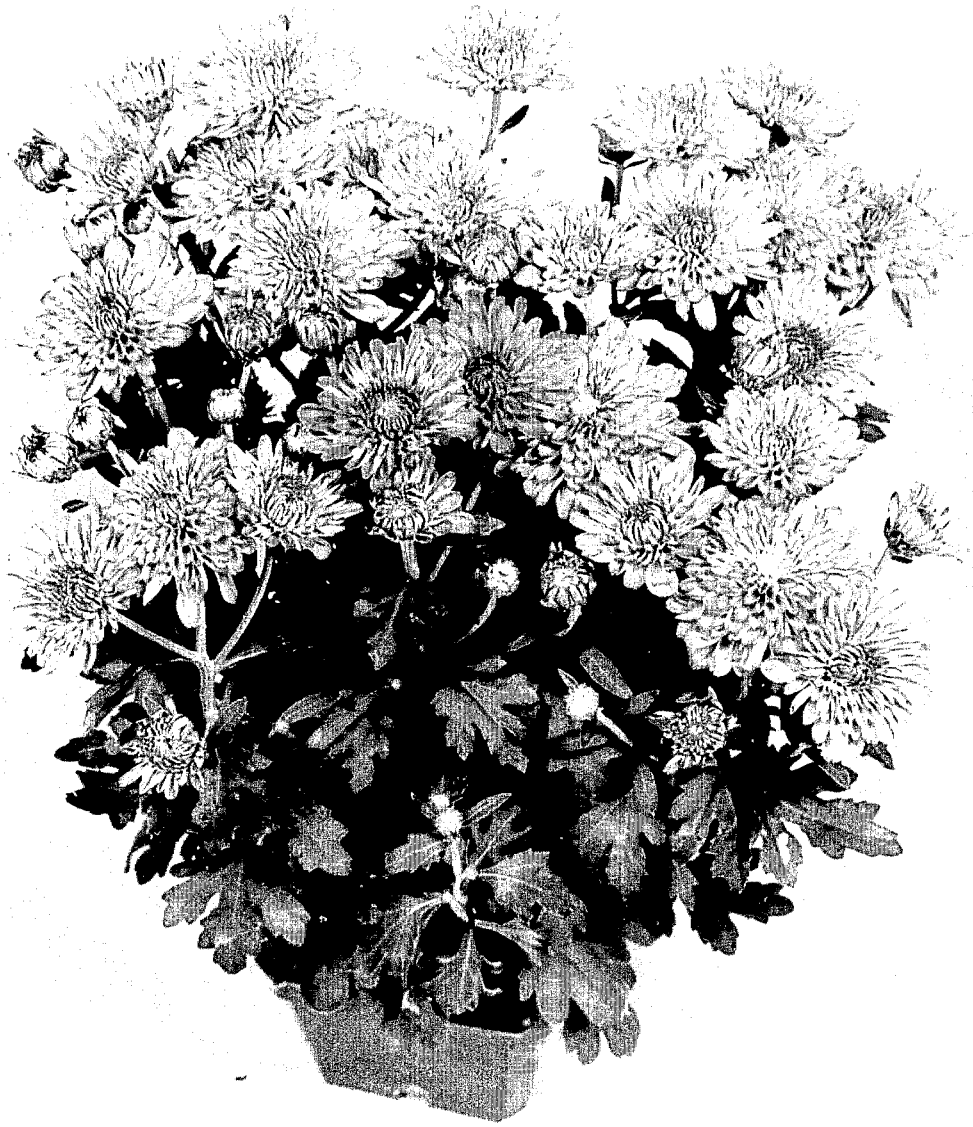

* * * * *